(12) United States Patent
Escaich Ferrer et al.

(10) Patent No.: US 8,394,781 B2
(45) Date of Patent: Mar. 12, 2013

(54) DISACCHARIDES FOR THE TREATMENT OF TENDONS, LIGAMENTS, AND BONES

(75) Inventors: Josep Escaich Ferrer, Barcelona (ES); Ana Maria Torrent Gibert, Barcelona (ES); Ramon Ruhi Roura, Barcelona (ES); Carlos Raul Alaez Verson, Blanes (ES)

(73) Assignee: Bioiberica, S.A., Barcelona (ES)

( * ) Notice: Subject to any disclaimer, the term of this patent is extended or adjusted under 35 U.S.C. 154(b) by 407 days.

(21) Appl. No.: 12/664,589

(22) PCT Filed: May 15, 2008

(86) PCT No.: PCT/EP2008/055959
§ 371 (c)(1),
(2), (4) Date: Dec. 14, 2009

(87) PCT Pub. No.: WO2008/151898
PCT Pub. Date: Dec. 18, 2008

(65) Prior Publication Data
US 2010/0129331 A1    May 27, 2010

(30) Foreign Application Priority Data
Jun. 15, 2007  (ES) .................................. 200701656

(51) Int. Cl.
*A61K 31/7016* (2006.01)
*A61K 31/715* (2006.01)
*A61K 31/737* (2006.01)
*A61K 31/70* (2006.01)

(52) U.S. Cl. ..... 514/53; 514/54; 536/123.13; 536/123.1

(58) Field of Classification Search .................... 514/53, 514/54; 536/123.13, 123.1
See application file for complete search history.

(56) References Cited

U.S. PATENT DOCUMENTS
2003/0181400 A1    9/2003    Vila Pahi et al.

FOREIGN PATENT DOCUMENTS
| EP | 1 300 411 B1 | 4/2003 |
| WO | 93/09766 A1 | 5/1993 |
| WO | 00/61592 A1 | 10/2000 |
| WO | WO 2005/084610 A2 * | 9/2005 |

OTHER PUBLICATIONS

Uebelhart et al (Osteoarthritis and Cartilage (1998) 6, (Supplement A), 39-46).*
Frizziero et al. (Clinical and Experimental Rheumatology 1998; 16:441-449).*
Hochberg et al. (Arthritis & Rheumatism vol. 37 No. 8, Aug. 1994, pp. 1177-1180).*
International Search Report of PCT/EP2008/055959 dated Aug. 5, 2008.

* cited by examiner

*Primary Examiner* — Shaojia Anna Jiang
*Assistant Examiner* — Michael C Henry
(74) *Attorney, Agent, or Firm* — Sughrue Mion, PLLC (57) ABSTRACT

Disaccharides for the treatment of tendons, ligaments and bones.

The present invention relates to the use of a series of disaccharides, as well as of compositions containing them, for the preparation of a medicament for the treatment or prevention of a tendon, ligament or bone disease, disorder or injury. The present invention also relates to the new compositions comprising a disaccharide in combination with inulin polysulphate, a glycosaminoglycan, a growth factor or cells. The glycosaminoglycan is preferably chondroitin sulphate or hyaluronic acid and the growth factor is IFG-1.

24 Claims, 6 Drawing Sheets

DISACCHARIDES FOR THE TREATMENT OF TENDONS, LIGAMENTS, AND BONES

TECHNICAL FIELD OF THE INVENTION

The present invention relates to the use of a series of disaccharides for the preparation of a medicament for the treatment or prevention of a tendon, ligament or bone disease, disorder or injury. The present invention likewise relates to new compositions comprising the disaccharides.

BACKGROUND OF THE INVENTION

A number of studies have confirmed that bones and soft tissues such as ligaments and tendons, especially in adult persons, have a limited self-repairing capacity.

The functional and structural properties of tendons and of ligaments are very similar. Tendons are anatomical structures attaching muscles to bones and ligaments are similar structures attaching bones to other bones. Both are cylindrical, elongated structures, formed from dense connective tissue and adapted to tension in one direction, with parallel collagen (mainly type I collagen) fibers. The reduced vascularization of said tissues is one of the causes of the slow healing of tendons and ligaments.

The predominant cells in tendons are called tenocytes. The function of tenocytes is to maintain the matrix structure through degradation and synthesis processes. However, tendons have a relatively low cell density and with little mitotic activity, which explains the reduced rate of replacement of this tissue and questions the degree in which these cells can promote intrinsic healing.

Tendon injuries are the commonest orthopedic injuries. For example, at least 100,000 Achilles tendon injuries are diagnosed and treated yearly in USA (A. Praemer et al., "Musculoskeletal condition in the United States", 1st ed. American Academy of Orthopaedic Surgeons, Park Ridge, Ill., 1992). It was also estimated that there were from 150,000 to 200,000 anterior cruciate ligament (ACL) injuries every year in the USA (S. L. Woo et al., "Contribution of biomechanics, orthopaedics and rehabilitation: the past present and future", *Surgeon* 2(3), 125-136 (2004)).

Damages in tendons and ligaments are caused by different factors, including injuries due to practicing sports or accidents, distensions, incorrect postures, bacterial infections, adverse drug reactions, arthritis in a joint, and as a result of different diseases.

The healing below the optimal level, the long rehabilitation period and a high incidence of relapse make it difficult to suitably treat tendon and ligament injuries.

The most frequent pharmacological treatments for tendinopathies (tendon diseases) and desmopathies (ligament diseases) include the following: rest, physical therapy (exercises, massages, ultrasound, laser, hydrotherapy, heat and cold), dietary supplements, surgery and medicaments, including nonsteroidal anti-inflammatory drugs (NSAIDs), glucocorticoids and antibiotics, the latter in the event that the disease has been caused by an infection. It is known that both NSAIDs and glucocorticoids have side-effects. The side-effects of NSAIDs include stomach acidity, nausea, diarrhea, dizziness and in some cases, gastric ulcers and liver inflammation. The side-effects of glucocorticoids can be bleeding, tendon rupture and infection, and can even slow down collagen synthesis. Furthermore, recent publications question the efficacy of NSAIDs in tendon regeneration (D. Marsolais et al., "Nonsteroidal anti-inflammatory drug reduces neutrophil and macrophage accumulation but does not improve tendon regeneration", *Lab. Invest.* 83(7), 991-999 (2003)).

In the last few years, investigations are being conducted on the treatment of tendinopathies and desmopathies with stem cells (R. G. Young et al., "Use of mesenchymal stem cells in a collagen matrix for Achilles tendon repair", *J. Orthop. Res.* 16(4), 406-413 (1998)), tenocytes (US 2005060033), ligament cells (J. A. Cooper, Jr., "Evaluation of the anterior cruciate ligament, medial collateral ligament, Achilles tendon and patellar tendon as cell sources for tissue-engineered ligament", *Biomaterials* 27, 2747-2754 (2006)), growth factors (WO 01/82951; L. A. Dahlgren et al., "Insulin-like growth factor-I improves cellular and molecular aspects of healing in a collagenase-induced model of flexor tendonitis", *J. Orthop. Res.* 20, 910-919 (2002)) or with genes (R. S. Goomer et al., "Nonviral in vivo gene therapy for tissue engineering of articular cartilage and tendon repair", *Clin. Orthop.* Oct (379 Suppl), S189-200 (2000)).

Bone tissue is a specialized connective tissue which, like the rest of connective tissues, is formed by cells, fibers and ground substance but, unlike the others, its extracellular components are calcified and make it a hard, firm material which is suitable for its support and protection function. It provides internal support to the body and offers insertion sites to muscles, tendons and ligaments which are essential for movement.

Bone defects represent a great medical and socioeconomic challenge. For example, the most recent investigations include the application of different types of biomaterials for reconstructing damaged bone tissues (U. Kneser, et al., Tissue engineering of bone: the reconstructive surgeon's point of view, *J. Cell. Mol. Med.* 10 (1), 7-19 (2006)), as well as the use of growth factors (WO 2006/044334) and stem cells (U.S. Pat. No. 6,863,900).

Bones, tendons and ligaments, mentioned above, are components of the musculoskeletal system, and all of them are derived at an embryonic level from the mesoderm.

The compounds of the present invention are disaccharides described for the first time in patent EP 1300411 (U.S. Pat. No. 6,680,304), with usefulness in the treatment of the osteoarthritis (arthrosis). Said patent document also mentions their usefulness in the treatment of inflammatory diseases such as inflammatory arthritis, rheumatoid arthritis, psoriatic arthritis, rheumatic fever, palindromic rheumatism, Reiter's syndrome, lupus erythematosus and ankylosing spondylitis, as well as in blood coagulation control. The basic structure of these compounds contains the monosaccharides glucuronic acid and glucosamine, bonded by means of β-(1→3) bonds, and with a sulphate group in C-4 and/or in C-6 of the monosaccharide glucosamine.

Glycosaminoglycans (GAG) forming part of some compositions of the present invention are polymeric biomolecules with a high molecular weight which are essentially located in live organisms, in which they develop different physiological functions.

Chondroitin sulphate is a natural sulphated glycosaminoglycan with a polymeric structure characterized by a disaccharide which is repeated, formed by N-acetyl-D-galactosamine and D-glucuronic acid. Most of the N-acetyl-D-galactosamine residues are sulphated. Chondroitin sulphate is an essential component of the aggrecan which is located in articular cartilage.

The use of chondroitin sulphate for treating different diseases, for example in the treatment of cardiovascular diseases (U.S. Pat. No. 3,895,106) or in the treatment of psoriasis (WO2005/014012), has been described, however, its most extended use is in the treatment of osteoarthritis, which is characterized by the degeneration of hyaline articular cartilage (M. G. Lequesne, *Rev. Rhum. Eng. Ed.*, 61, 69-73 (1994); G. Verbruggen et al., *Osteoarthritis Cart.*, 6 (Supplement A), 37-38 (1998)).

Hyaluronic acid is a non-sulphated glycosaminoglycan with a polymeric structure characterized by a disaccharide which is repeated, formed by the monosaccharides N-acetyl-D-glucosamine and D-glucuronic acid. It is one of the main components of cartilage, of the synovial membrane and of synovial fluid. Its use in the treatment of osteoarthritis, generally intra-articularly, is particularly important. Its use in ophthalmology for speeding up wound healing, as well as in cosmetics, has also been described.

Contradictory results have been published on the use of chondroitin sulphate, of chondroitin polysulphate and of hyaluronic acid in the treatment of tendinopathies. Although some authors describe the beneficial effect of said compounds (E. M. Gaughan et al., "Effects of sodium hyaluronate on tendon healing and adhesion formation in horses", *Am. J. Vet. Res.* 52(5), 764-773 (1991); H. Sundqvist et al., "A promising novel therapy for Achilles peritendinitis", *Int. J. Sports Med.* 8, 298-303 (1987)), other authors, however, do not find significant differences between treated tendons and the control group (S. J. Dyson, "Medical management of superficial digital flexor tendonitis: a comparative study in 219 horses (1992-2000)", *Equine Vet. J.* 36(5), 415-419 (2004); J. W. Foland et al., "Effect of sodium hyaluronate in collagenase-induced superficial digital flexor tendinitis in horses", *Am. J. Vet. Res.* 53(12), 2371-2376 (1992)).

Inulin polysulphate, forming part of the compositions of the invention, is obtained from the natural polysaccharide inulin. The alkaline salts of inulin sulphate with different degrees of sulphation have been applied in the chemical industry as thickeners, adhesives and as additives for muds used in oil well drilling. It has been described that inulin sulphate has an anticoagulant (*Arkiv for kemi, mineralogi o. geologi., Bd* 24B (5), 1-4 (1946)) and antilipidemic activity (*Arch. Int. Pharmacodyn, XCIX,* 334 (1954)).

It has been described that inulin polysulphate (U.S. Pat. No. 4,021,545) has a complement inhibitory activity; therefore it could be used in the treatment of diseases such as rheumatoid arthritis, systemic lupus erythematosus and certain types of vasculitis. Its use in the treatment of osteoarthritis has also been described (WO 2005/084610).

According to the above, it was necessary to provide an alternative drug useful in the treatment or prevention of a tendon, ligament or bone disease, disorder or injury.

The use of the disaccharides of the present invention in the treatment of tendons, ligaments or bones has not been described up until now.

The compositions of the present invention comprising the disaccharides have not been described either.

DISCLOSURE OF THE INVENTION

It has unexpectedly now been observed that the compounds described in patent EP 1300411 are useful in the treatment of a tendon, ligament or bone disease, disorder or injury.

The present invention thus relates to the use of a compound of formula (I):

wherein:
$R^1$ is hydrogen, linear or branched $C_1$-$C_4$ alkyl, phenylalkyl of less than ten carbon atoms or —$COCH_3$;
$R^2$ is hydrogen, —$COCH_3$ or —$SO_3Y$;
$R^3$ is hydrogen, linear or branched $C_1$-$C_4$ alkyl, phenylalkyl of less than ten carbon atoms, —$COCH_3$ or —$COPh$, wherein Ph is phenyl;
G is —$COOR^4$ or —COOY, wherein $R^4$ is hydrogen, $C_1$-$C_2$ alkyl or arylalkyl of less than sixteen carbon atoms;
A is hydrogen, —$SO_3H$, —$SO_3Y$ or —$COCH_3$; and
B is hydrogen, —$SO_3H$, —$SO_3Y$, or —$COCH_3$, wherein either A or B is necessarily either —$SO_3H$ or —$SO_3Y$, wherein Y is an organic or inorganic cation; as well as the solvates and the pharmaceutically acceptable salts thereof, for the preparation of a medicament for the treatment or prevention of a tendon, ligament or bone disease, disorder or injury in a mammal.

In the present invention the term "treatment" includes tendon, ligament or bone repair or regeneration.

The compounds of formula (I) comprise an anomeric carbon in their structure. The invention includes both the mixtures and the separate anomeric forms α and β.

In a preferred embodiment, the compounds of formula (I) are those wherein: $R^1$ is hydrogen or linear $C_1$-$C_4$ alkyl and G is —$COOR^4$ or —COOY, wherein $R^4$ is hydrogen or $C_1$-$C_2$ alkyl and Y is an inorganic cation.

In a more preferred embodiment, the compounds of formula (I) are those wherein: $R^1$ is hydrogen, $R^2$ is —$COCH_3$ and $R^3$ is hydrogen. The compounds of formula (I) wherein $R^1$ is methyl, $R^2$ is —$COCH_3$ and $R^3$ is hydrogen are likewise preferred.

In a particularly preferred embodiment, the compounds of formula (I) are those wherein: A is hydrogen, B is —$SO_3Y$ and G is —COOY, wherein Y is an inorganic cation. The compounds of formula (I) wherein: A is —$SO_3Y$, B is hydrogen and G is —COOY, wherein Y is an inorganic cation, are also particularly preferred. The compounds of formula (I) wherein: A and B are —$SO_3Y$ and G is —COOY, wherein Y is an inorganic cation, are likewise particularly preferred.

An especially preferred individual compound of the invention is: methyl 2-acetamido-2-deoxy-3-O-(β-D-glucopyranosyluronic acid)-4-O-sulfo-α-D-glucopyranoside, disodium salt, of formula:

Another especially preferred individual compound of the invention is: methyl 2-acetamido-2-deoxy-3-O-(β-D-glucopyranosyluronic acid)-6-O-sulfo-α-D-glucopyranoside, disodium salt, of formula:

Another especially preferred individual compound of the invention is: methyl 2-acetamido-2-deoxy-3-O-(β-D-glucopyranosyluronic acid)-4,6-di-O-sulfo-α-D-glucopyranoside, trisodium salt, of formula:

The ligament is preferably an articular or periodontal ligament and the bone is a periodontal bone.

In another preferred embodiment, the medicament further comprises a glycosaminoglycan, preferably chondroitin sulphate, hyaluronic acid or dermatan sulphate.

In another also preferred embodiment, the medicament further comprises inulin polysulphate.

In another also preferred embodiment, the medicament further comprises a growth factor, preferably IGF-1.

In another also preferred embodiment, the medicament further comprises cells selected from the group consisting of tenocytes, epitenon cells, ligament cells, periodontal ligament fibroblasts, cementoblasts, osteoblasts, osteocytes and stem cells.

The disease, disorder or injury is preferably selected from the group consisting of tendinosis, tendinitis (tendonitis), rheumatoid tendinitis, peritendinitis, tenosynovitis, paratenonitis, bone loss, periodontitis, gingivitis associated to periodontitis and any desmopathy. Likewise, the disease, disorder or injury is the result of a trauma, an overuse or a pathological condition, an infectious, metabolic or endocrine disease, for example.

The medicament is preferably suitable for oral, intralesional, perilesional, intra-articular administration, for administration in an implant or for topical administration to an exposed tendon, ligament or bone.

The present invention also describes pharmaceutical compositions comprising a compound represented by formula (I) and a glycosaminoglycan. The glycosaminoglycan is preferably chondroitin sulphate or hyaluronic acid.

The pharmaceutical compositions comprising a compound represented by formula (I) and inulin polysulphate are also preferred.

The pharmaceutical compositions comprising a compound represented by formula (I) and a growth factor are also preferred. The growth factor is preferably IGF-1.

The pharmaceutical compositions comprising a compound represented by formula (I) and cells selected from the group consisting of tenocytes, epitenon cells, ligament cells, periodontal ligament fibroblasts, cementoblasts, osteoblasts, osteocytes and stem cells are also preferred.

Especially preferred is the pharmaceutical composition in which the compound of formula (I) is: methyl 2-acetamido-2-deoxy-3-O-(β-D-glucopyranosyluronic acid)-4-O-sulfo-α-D-glucopyranoside, disodium salt, of formula:

Likewise, especially preferred is the pharmaceutical composition in which the compound of formula (I) is: methyl 2-acetamido-2-deoxy-3-O-(β-D-glucopyranosyluronic acid)-6-O-sulfo-α-D-glucopyranoside, disodium salt, of formula:

Likewise, especially preferred is the pharmaceutical composition in which the compound of formula (I) is: methyl 2-acetamido-2-deoxy-3-O-(β-D-glucopyranosyluronic acid)-4,6-di-O-sulfo-α-D-glucopyranoside, trisodium salt, of formula:

The present invention also relates to a compound represented by formula (I) defined above, or a solvate or a pharmaceutically acceptable salt thereof, for its use in the treatment or prevention of a tendon, ligament or bone disease, disorder or injury in a mammal.

The preparation of the compounds of formula (I) according to the present invention can be carried out according to the synthetic routes described in patent EP 1300411.

Depending on the nature of cation Y (organic or inorganic, metal cations preferably being among the latter), organic or inorganic salts will be obtained. Examples of inorganic salts include sodium, potassium, calcium, magnesium, aluminium, ammonium and lithium salts, for example. Examples of organic salts include ethanolamine, triethanolamine and basic amino acid salts, for example.

The pharmaceutical compositions according to the present invention can comprise the compounds of formula (I) and a glycosaminoglycan, such as chondroitin sulphate, hyaluronic acid or dermatan sulphate.

Chondroitin sulphate, a component of some compositions of the present invention, is a sulphated glycosaminoglycan with a molecular weight comprised between 10,000 daltons and 60,000 daltons, depending on the origin and process for obtaining it. It is obtainable from animal cartilaginous tissues, such as porcine or bovine cattle tracheas, and shark cartilaginous skeleton, according to processes described in the literature (ES 547769). Its polymeric structure is characterized by a disaccharide which is repeated, formed by N-acetylgalactosamine and D-glucuronic acid. Most of the N-acetylgalactosamine residues are sulphated.

Chondroitin sulphate from cartilaginous issue is mainly found in two isomeric forms differing in the position of the sulphate group present in the N-acetylgalactosamine residue, chondroitin 4-sulphate (chondroitin sulphate A) and chondroitin 6-sulphate (chondroitin sulphate C), which are represented by the following structure:

$R^1 = SO_3^-Na^+, R^2 = H$
$R^2 = SO_3^-Na^+, R^1 = H$

In addition to chondroitin 4-sulphate and chondroitin 6-sulphate, the term chondroitin sulphate also includes the following compounds: chondroitin sulphate B, also known as dermatan sulphate; chondroitin sulphate D, known as chondroitin 2,6-disulphate; chondroitin sulphate E, known as chondroitin 4,6-disulphate.

In the present invention, the term "chondroitin sulphate" covers all these compounds, as well as mixtures thereof.

The hyaluronic acid used in the compositions of the present invention is a non-sulphated glycosaminoglycan with a molecular weight comprised between 100,000 daltons and 3,000,000 daltons. It is obtainable, by means of extraction, from bird or mammalian tissues, from vitreous humor, mammalian skin, umbilical cord, bird crests for example, and by fermentation of microorganisms, Streptococcus for example, according to processes described in the literature (D. A. Swann, *Biochim. Biophys. Acta* 156, 17-30 (1968); U.S. Pat. No. 4,780,414).

Its polymeric structure is characterized by a disaccharide which is repeated, formed by N-acetyl-D-glucosamine and D-glucuronic acid:

Inulin polysulphate, which is a component of some compositions used in the present invention, is obtainable by sulphonation of the free hydroxyl groups present in the structure of the natural polysaccharide inulin, according to processes described in the literature (WO 2005/084610). It is represented by means of the following structure:

$R = SO_3^-Na^+$

Dermatan sulphate, also called chondroitin sulphate B, is obtainable from bird or mammalian tissues, from bovine or porcine mucous membranes and bird crests for example, according to processes described in the literature (N. Volpi, *Anal. Biochem.* 218, 382-391 (1994); U.S. Pat. No. 5,116, 963).

When the present invention mentions growth factors, it refers to growth factors having an important role in bone, tendon or ligament growth, These growth factors particularly include, among others, IGF-1 (Insulin-like Growth Factor 1) and BMP-2 (Bone Morphogenetic Protein 2).

When the present invention mentions stem cells, it refers to both embryonic stem cells and to adult stem cells. The latter include mesenchymal cells.

When the present invention mentions intralesional administration, it refers to the direct administration in the actual injury.

When the present invention mentions perilesional administration, it refers to the administration around the injury.

For the use in the treatment or prevention of a tendon, ligament or bone disease, disorder or injury, the compounds of the invention are formulated in suitable pharmaceutical compositions, using conventional techniques and excipients or carriers, such as those described in *Remington: The Science and Practice of Pharmacy* 2000, edited by Lippincott Williams and Wilkins, 20th edition, Philadelphia.

The pharmaceutical compositions of the invention can be administered to the patient in required doses. The administration of the compositions can be carried out through different routes, for example, oral, intravenous, intraperitoneal, intra-articular, intralesional, perilesional, intratendinous, peritendinous, intrathecal, subcutaneous, intramuscular, topical, sublingual, intradermal or intranasal. The pharmaceutical compositions of the invention include a therapeutically effective amount of active component, said amount depending on many factors, such as for example the physical condition of the patient, age, sex, particular compound, route of administration, severity of the symptoms and on other factors that are well known in the art. Furthermore, it will be understood that said dosage of active component can be administered in single or multiple dose units to provide the desired therapeutic effects.

The pharmaceutical preparations of the invention will generally be in solid, liquid form or as a gel. The pharmaceutical preparations in solid form that can be prepared according to the present invention include powders, pellets, microspheres, nanoparticles, tablets, dispersible granules, capsules, seals and suppositories. The preparations in liquid form include solutions, suspensions, emulsions, syrups and elixirs. The preparations in solid form which are to be converted, immediately before being used, into preparations in liquid form are also contemplated. Said liquid forms include solutions, suspensions and emulsions.

According to the present invention, it has been found that the use of the compounds of the invention has advantages such as: (i) in an in vitro assay for measuring the stimulation of human tenocyte proliferation and adhesion, their action is faster than that of the growth factor IGF-1; (ii) the absence of toxic effects on tenocytes since, after the assay, the tenocytes have a large amount of endoplasmic reticulum and extracellular matrix and (iii) the expression of type I collagen and of the adhesion molecule β1-integrin is not altered.

In the figures and examples described below, Ic is a compound of formula:

Ic

DETAILED DESCRIPTION OF THE PREFERRED EMBODIMENTS

The following examples are merely illustrative and do not represent a limitation of the scope of the present invention.

Example 1

Effect of Compound Ic on Human Tenocyte Adhesion and Proliferation

The objective was to determine the effect of compound Ic on human tenocyte proliferation and adhesion in an in vitro culture model, since a drug stimulating tenocyte proliferation and adhesion could be especially useful in the treatment or repair of tendons.

For comparison purposes, the effect of the growth factor IGF-1 on human tenocyte proliferation and adhesion in the same type of in vitro culture model was determined.

The increase of adhered tenocytes was quantified by means of manual count in ten microscopic fields.

Materials and Methods of Example 1:

Human tendon explants (of approximately 3-5 mm) were cultured in a culture flask with culture medium formed by 10% FCS, DMEM/Ham-12 (50/50) (Dulbecco's Modified Eagle's Medium with Ham-12), 50 IU/mL of penicillin/streptomycin, 25 g/mL of ascorbic acid, 2.5 μg/mL of amphotericin B, 1% glutamine and 1% essential amino acids. After 1-2 weeks, the tenocytes started to migrate from the tendon tissue, adhering to the culture flask and forming a monolayer. Several passages were carried out until gaining a sufficient amount of tenocytes.

Twelve-well plates were prepared with 15,000 tenocytes/well and they were incubated with 10% FCS (fetal calf serum). On the following day, the cells were washed three times with serum-free culture medium (0.5% FCS) and were incubated for 30 minutes with serum-free culture medium, after which the control cultures were counted (time "0 hours"). The compound Ic to be assayed (the assay was carried out at three concentrations: 200, 1,000 and 3,000 μg/mL) was added and the cells were incubated using a serum-free culture medium (only 0.5% FCS). The control culture and the growth factor IGF-1 culture (10 ng/mL) were also incubated in serum-free culture medium.

In all the assays, the cells were incubated for 71 hours and each well was evaluated in each time period by means of a manual count in 10 microscopic fields.

Figure 1:
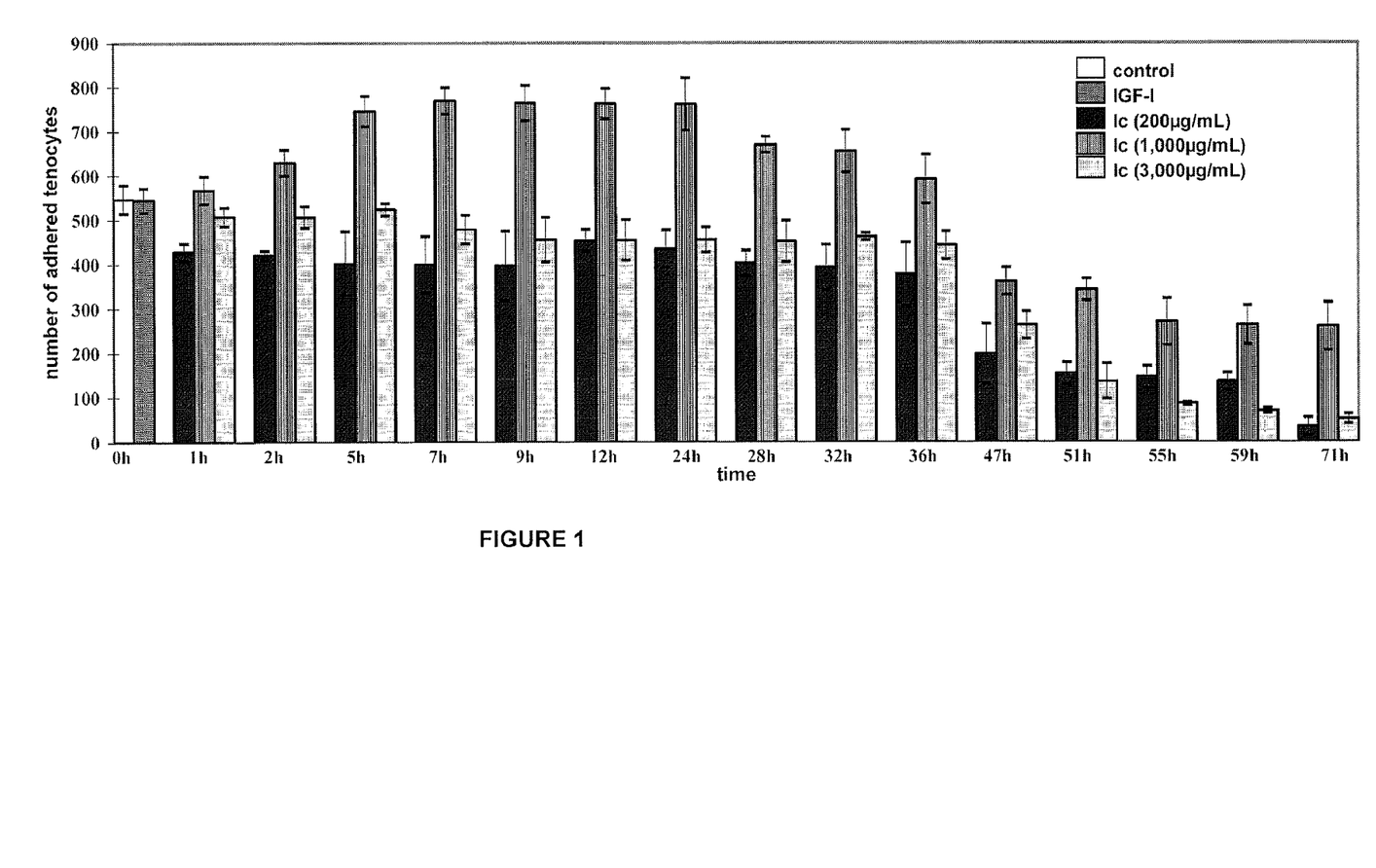
FIG. 1 shows, at three concentrations (200, 1,000 and 3,000 μg/mL), the effect of compound Ic on the number of adhered human tenocytes throughout 71 hours. The control and IGF-1 at time zero are also included.
Figure 2:
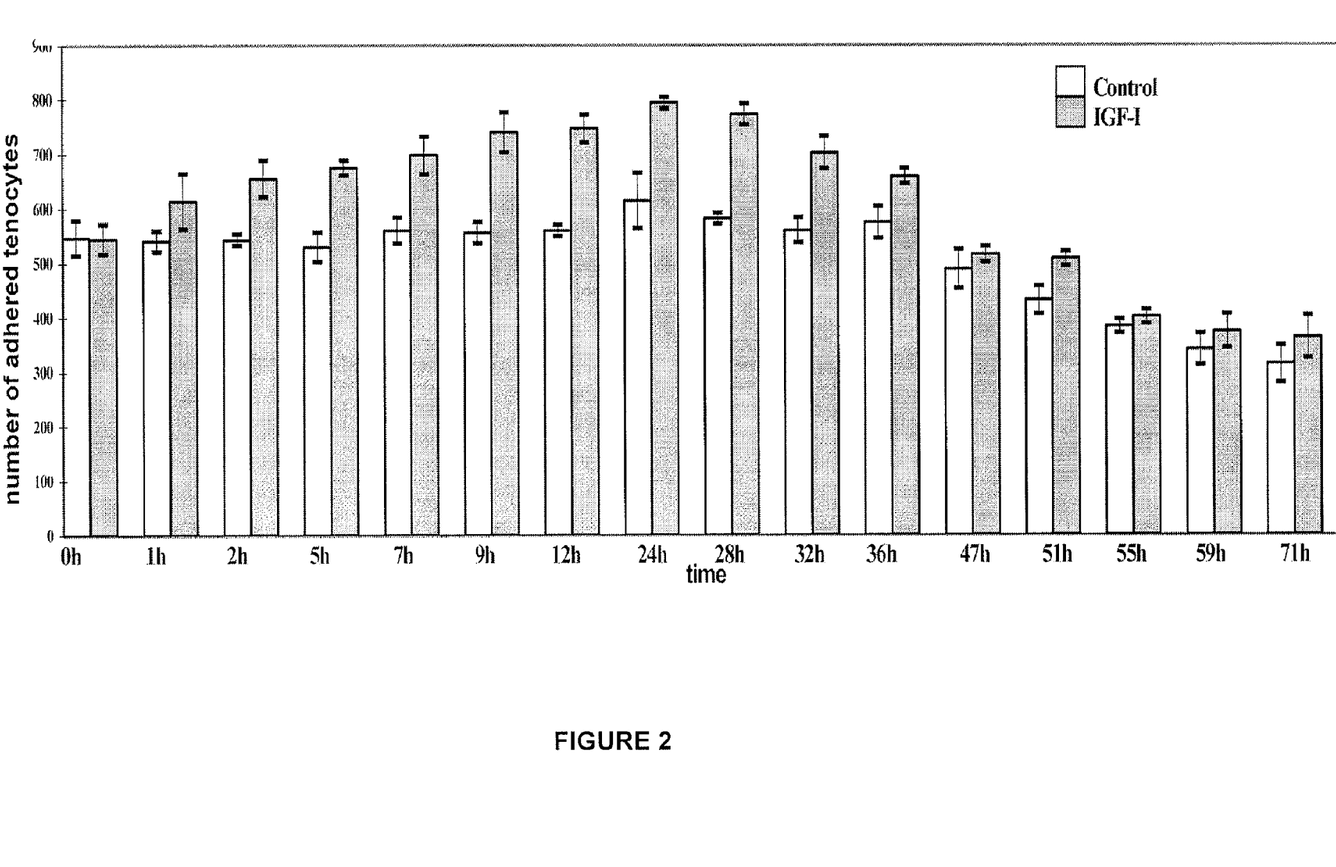
FIG. 2 shows the effect of the growth factor IGF-1 and of the control (culture in the absence of compound) on the number of adhered human tenocytes throughout 71 hours.

Results of Example 1:

Of the three assayed concentrations of compound Ic of the invention, the optimal concentration is 1,000 μg/mL (FIG. 1). At this concentration and after 5 hours, compound Ic causes an increase of the order of 45% in the number of adhered tenocytes with respect to the control (without compound), this level is maintained up to 24 hours, whereas this same increase is reached after 9 hours in the case of IGF-1 (FIG. 2).

It can be concluded that compound Ic of the invention stimulates human tenocyte proliferation and adhesion, its action being faster than that of IGF-1.

Example 2

Effect of a Mixture of Chondroitin Sulphate and Compound Ic on Human Tenocyte Adhesion and Proliferation The methodology described in Example 1 was followed, but in this case 12-well plates were prepared with 10,000 tenocytes/well. The mixture of chondroitin sulphate and compound Ic (CS/Ic) was assayed at three concentrations: 500/500, 1,000/200 and 1,000/500 μg/mL.

Figure 9:
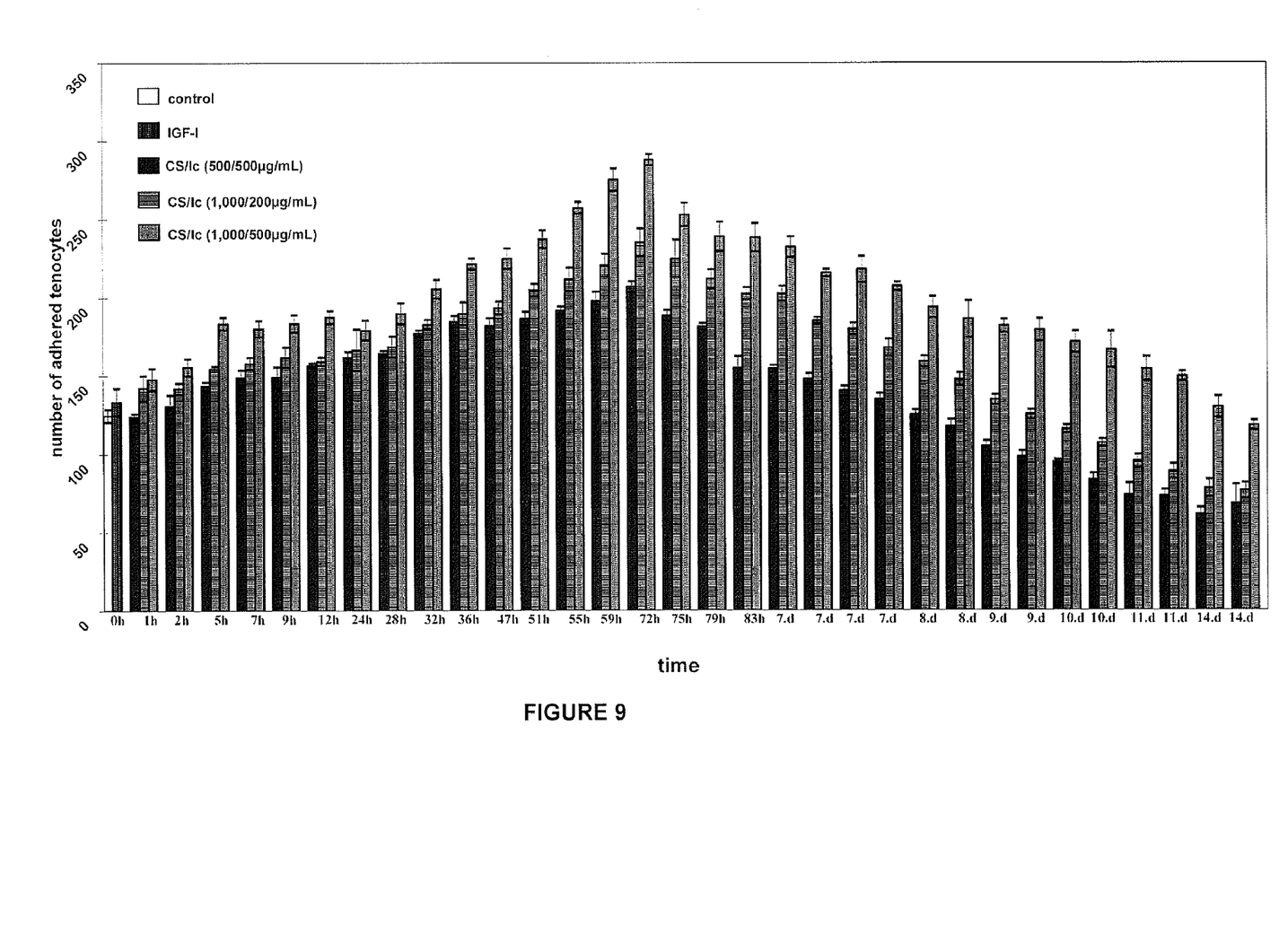
FIG. 9 shows, at three concentrations (500/500, 1,000/200 and 1,000/500 μg/mL) the effect of a mixture formed by chondroitin sulphate and compound Ic (CS/Ic) on the number of adhered human tenocytes throughout 14 days. The control and IGF-1 at time zero are also included.

Results of Example 2:

Of the three assayed concentrations of the mixture formed by chondroitin sulphate and compound Ic (CS/Ic), the optimal concentration is 1,000/500 µg/mL (FIG. 9). At this concentration and after 72 hours, the CS/Ic mixture causes an increase of the order of 33% in the number of adhered tenocytes with respect to the control (without compound), it can therefore be concluded that said mixture stimulates human tenocyte proliferation and adhesion.

Example 3

Evaluation of the Tenocytes by Transmission Electron Microscopy after being Incubated with Compound Ic The objective was to observe the vitality and the signs of apoptosis of the cells after one hour of incubation without compound (control) or with the compound Ic of the invention, in order to be able to determine the toxicity of the compound of the invention.

Materials and Methods of Example 3:

The sufficient amount of tenocytes in a monolayer was prepared according to the methodology described in Example 1. Then 100,000 tenocytes per 35 mm Petri dish were seeded with 4 mL of culture medium formed by 10% FCS, DMEM/Ham-12 (50/50) (Dulbecco's Modified Eagle's Medium with Ham-12), 50 IU/mL of penicillin/streptomycin, 25 µg/mL of ascorbic acid, 2.5 µg/mL of amphotericin B, 1% glutamine and 1% essential amino acids, and they were incubated until reaching confluence. The cells were washed three times with serum-free medium (0.5% FCS) and were incubated for 30 minutes with this same medium. Before adding the compound to be assayed, a control was prepared at 0 hours by means of Karnovsky's fixative solution. The compound Ic to be assayed (it was assayed at three concentrations: 200, 1,000 and 3,000 µg/mL) was then added and cells were incubated with serum-free culture medium for 1 hour. The control culture and the IGF-1 culture (10 ng/mL) were also incubated with serum-free culture medium. The cells were washed three times with PBS and were treated with Karnovsky's fixative solution. The cells were then removed from the Petri capsule with a Cell-Scraper®, they were introduced in an Eppendorf tube and were centrifuged for 5 minutes at 400 g. The pellet of cells was then dehydrated with alcohol and it was subsequently fixed for 1 hour with 2% $OsO_4$. After an additional dehydration with alcohol, the pellet of cells was embedded in Epon. Ultrafine sections were made and were contrasted with uranyl acetate. The sections were examined under a transmission electron microscope (Zeiss).

Figure 3:
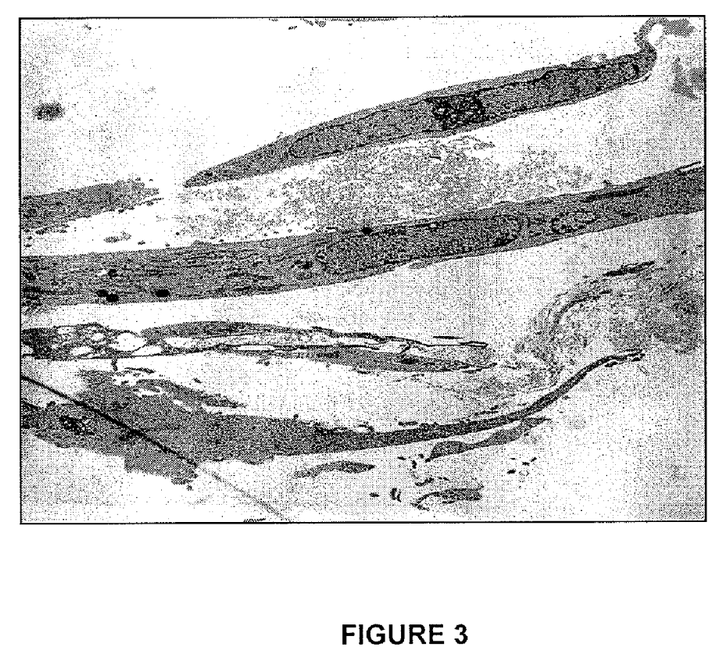
FIG. 3 displays human tenocytes by transmission electron microscopy, after their culture for 1 hour in the absence of compound (control).
Figure 4:
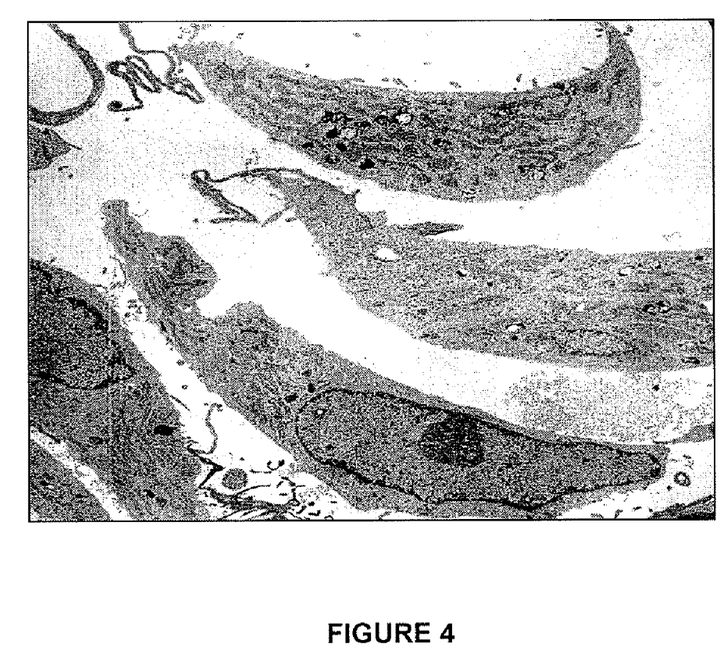
FIG. 4 displays human tenocytes by transmission electron microscopy, after their incubation for 1 hour with compound Ic.

Results of Example 3:

As can be observed by comparing FIGS. 3 (control, without compound) and 4 (with compound), no toxic effect is observed on the tenocytes after one hour of culture in the presence of compound Ic, which does not exert any catabolic effect on the tenocytes, since they have a large amount of endoplasmic reticulum and extracellular matrix.

Example 4

Evaluation of the Tenocytes by Transmission Electron Microscopy after being Incubated with a Mixture of Chondroitin Sulphate and compound Ic The methodology described in Example 3 was followed. The mixture formed by chondroitin sulphate and compound Ic (CS/Ic) was assayed at the concentration of 500/500 µg/mL.

Results of Example 4:

No toxic effect was observed on the tenocytes after one hour of culture in the presence of the mixture of chondroitin sulphate and compound Ic.

Example 5

Determination of Type I Collagen and of β1-Integrins by Immunofluorescence after Incubating Human Tenocytes with Compound Ic The objective was to determine the expression of type I collagen and of the adhesion molecule β1-integrin by human tenocytes, after their incubation for 1 hour with compound Ic of the invention and in the absence of compound (control).

Type I collagen is found both in tendons and in ligaments and is responsible for their resistance to tension, Healthy tendons mostly have type I collagen, with small amounts of type III collagen. Nevertheless, in a problem of tendinosis, for example, part of the collagen is lost and the structure is repaired by synthesizing type III collagen (incomplete tendon architecture). It is therefore desirable for type III collagen to be replaced by type I collagen in the regeneration process.

β1-integrins are membrane receptors allowing the cells to bind and respond to the extracellular matrix (adhesion). They are therefore necessary to maintain the proliferation, differentiation and survival properties of tenocytes.

Materials and Methods of Example 5:

A sufficient amount of tenocytes in a monolayer was prepared according to the methodology described in Example 1. Approximately 5,000 tenocytes per well were then seeded in 8-well Nunc culture plates. They were incubated overnight with culture medium formed by 10% FCS, DMEM/Ham-12 (50/50) (Dulbecco's Modified Eagle's Medium with Ham-12), 50 IU/mL of penicillin/streptomycin, 25 µg/mL of ascorbic acid, 2.5 µg/mL of amphotericin B, 1% glutamine and 1% essential amino acids. On the following day, the cells were washed three times with serum-free medium (0.5% FCS) and were incubated for 30 minutes with this same medium. The compound Ic to be assayed (it was assayed at three concentrations: 200, 1,000 and 3,000 µg/mL) was added and the cells were incubated using serum-free culture medium (only 0.5% FCS). The control and IGF-1 (10 ng/mL) cultures were also carried out with serum-free culture medium. After 1 hour of incubation, the cells were washed three times with PBS and fixed with methanol for 10 minutes at room temperature.

The following methodology was applied for the immunofluorescence labeling: the cells were incubated for 30 minutes with PBS (phosphate buffered saline)+1% BSA (bovine serum albumin), the primary antibody was diluted 1:50 in PBS+1% BSA (type I collagen, Chemicon, PAB; β1-integrin, Sigma, MAB) and the cells were incubated with said antibody in a wet chamber at 37° C. (2 hours MAB, 1 hour PAB). The cells were subsequently washed with PBS under stirring and the secondary antibody was diluted 1:50 in PBS+1% BSA (FITC-GAM or FITC-GAR, Dianova). The cells were incubated with the secondary antibody for 2 hours in a wet chamber. After this time, the cells were washed with PBS under stirring (in the absence of light) and were treated with Mowiol mounting medium (Fluka). They were subsequently examined under a fluorescence microscope.

Figure 5:
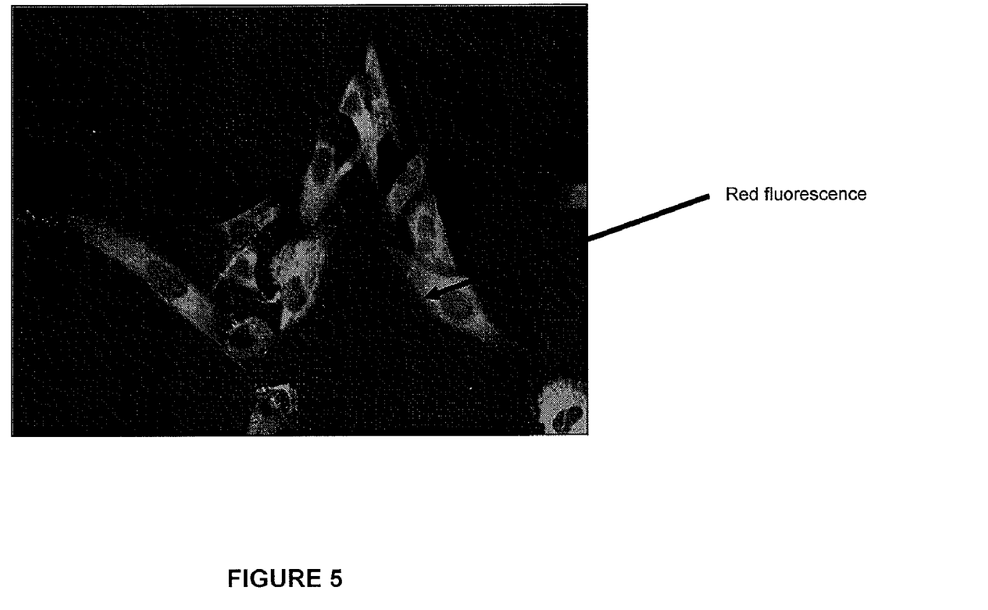
FIG. 5 displays, by red immunofluorescence, the expression of type I collagen by human tenocytes cultured in the absence of compound (control).
Figure 6:
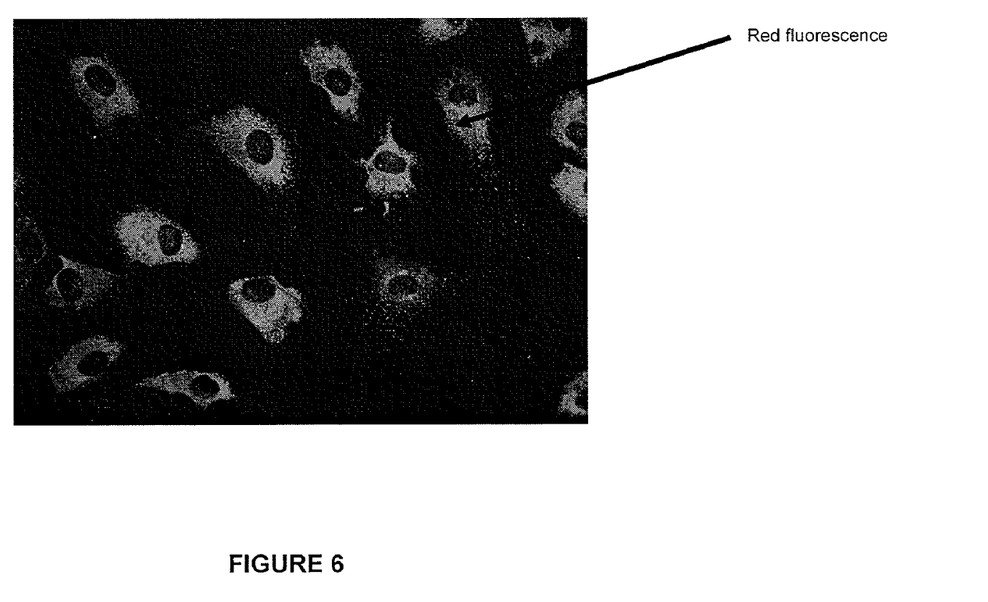
FIG. 6 displays, by red immunofluorescence, the expression of type I collagen by human tenocytes after their incubation for 1 hour with compound Ic.

Results of Example 5:

As can be observed in FIG. 6, the tenocytes continue to express type I collagen after one hour of culture in the presence of compound Ic. Differences with respect to the control (FIG. 5) are not observed.

Figure 7:
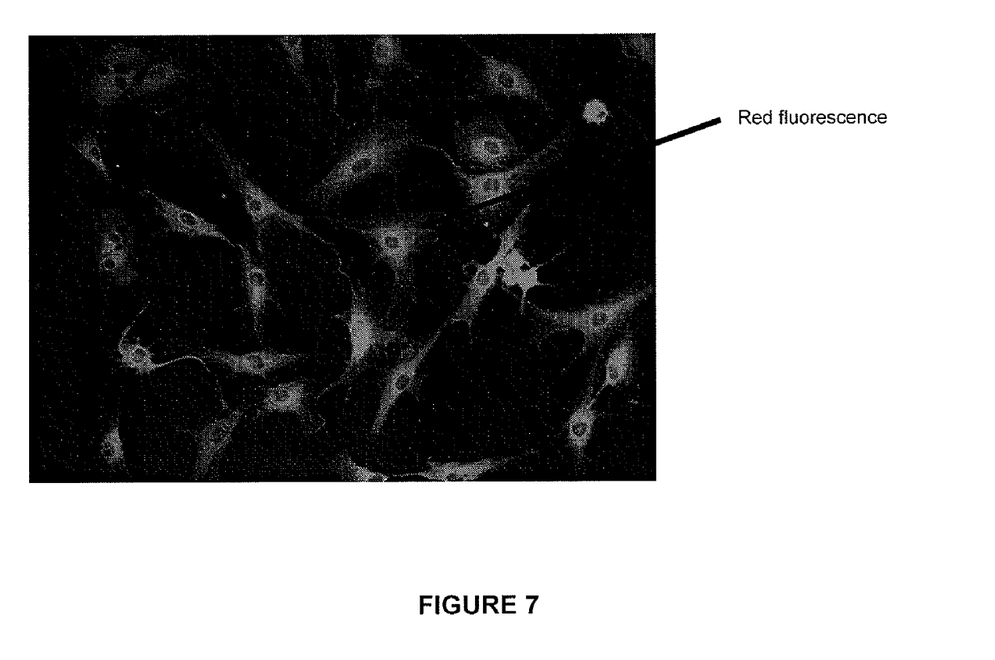
FIG. 7 displays, by red immunofluorescence, the expression of the adhesion molecule β1-integrin by human tenocytes cultured in the absence of compound (control).
Figure 8:
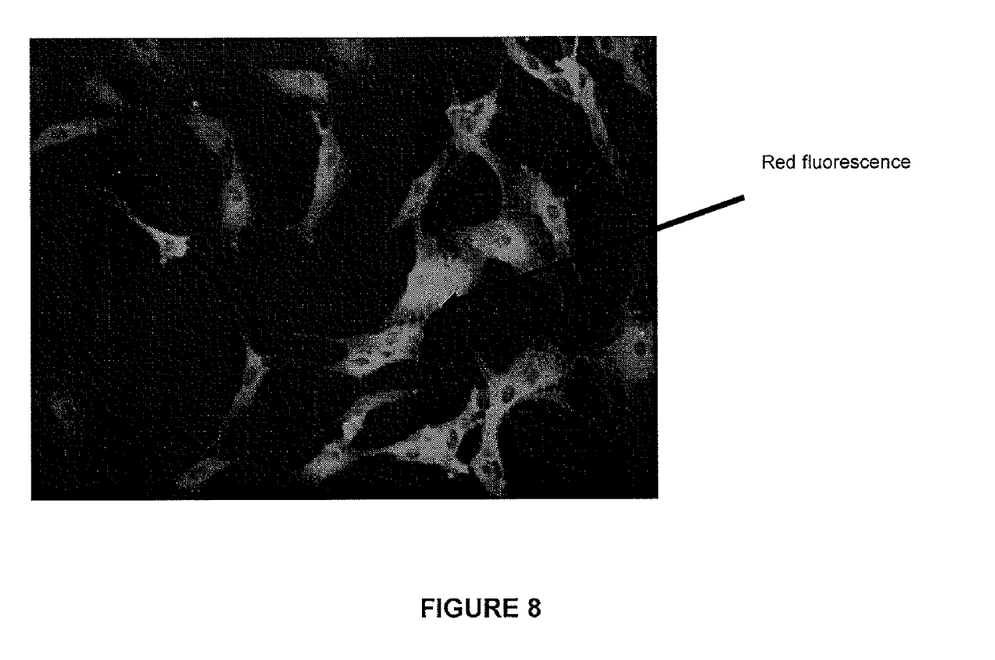
FIG. 8 displays, by red immunofluorescence, the expression of the adhesion molecule β1-integrin by human tenocytes after their incubation for 1 hour with compound Ic.

FIG. 8 shows the expression of the adhesion molecule β1-integrin after one hour of culture in the presence of compound Ic. Differences with respect to the control (FIG. 7) are not observed.

In all the determinations it was observed that the cells maintained the typical elongated morphology of healthy tenocytes.

Example 6

Determination of Type I Collagen and of β1-Integrins by Immunofluorescence after Incubating Human Tenocytes with a Mixture of Chondroitin Sulphate and Compound Ic The methodology described in Example 5 was followed, but in this case 2,500 tenocytes per well were seeded. The mixture of chondroitin sulphate and compound Ic (CS/Ic) was assayed at the concentration of 500/500 μg/mL.

Results of Example 6:

After one hour of culture with the mixture of chondroitin sulphate and compound Ic, the tenocytes continued to express type I collagen and the adhesion molecule β1-integrin. Differences with respect to the control (healthy human tenocytes incubated in the absence of the CS/Ic mixture) were not observed.

In all the determinations it was observed that the cells maintained the typical elongated morphology of healthy tenocytes.

Example 7

Tablets of Chondroitin Sulphate and Compound Ic

The tablets were prepared according to conventional processes.
Content of active ingredients per tablet:

| | |
|---|---|
| Chondroitin sulphate, sodium salt | 400.0 mg |
| Compound Ic | 400.0 mg |

Example 8

Injectable of Chondroitin Sulphate and Compound Ic 2 mL of injectable formulation were prepared according to conventional processes.
Content of active ingredients per mL:

| | |
|---|---|
| Chondroitin sulphate, sodium salt | 75 mg/mL |
| Compound Ic | 75 mg/mL |

Example 9

Injectable of Hyaluronic Acid and Compound Ic

2 mL of injectable formulation were prepared according to conventional processes.

Content of active ingredients per mL:

| | |
|---|---|
| Sodium hyaluronate | 5 mg/mL |
| Compound Ic | 100 mg/mL |

The invention claimed is:

1. A method of treating a tendon, ligament or periodontal bone disease, disorder or injury in a mammal comprising administering to a mammal in need thereof an effective amount of a compound of formula (I), wherein:
$R^1$ is hydrogen, linear or branched $C_1$-$C_4$ alkyl, phenylalkyl of less than ten carbon atoms or —$COCH_3$;
$R^2$ is hydrogen, —$COCH_3$ or —$SO_3Y$;
$R^3$ is hydrogen, linear or branched $C_1$-$C_4$ alkyl, phenylalkyl of less than ten carbon atoms, —$COCH_3$ or —COPh, wherein Ph is phenyl;
G is —$COOR^4$ or —COOY, wherein $R^4$ is hydrogen, $C_1$-$C_2$ alkyl or arylalkyl of less than sixteen carbon atoms;
A is hydrogen, —$SO_3H$, —$SO_3Y$ or —$COCH_3$; and
B is hydrogen, —$SO_3H$, —$SO_3Y$, or —$COCH_3$,
wherein either A or B is necessarily either —$SO_3H$ or —$SO_3Y$, wherein Y is an organic or inorganic cation, solvates, or pharmaceutically acceptable salts thereof,
with the proviso that said tendon, ligament or periodontal bone disease, disorder or injury is not an inflammatory disease, disorder or injury.

2. The method according to claim 1, which is for the treatment of a tendon disease, disorder or injury.

3. The method according to claim 1, which is for the treatment of a ligament disease, disorder or injury.

4. The method according to claim 1, which is for the treatment of a periodontal bone disease, disorder or injury.

5. The method according to claim 1, wherein $R^1$ is hydrogen or linear $C_1$-$C_4$ alkyl and G is —$COOR^4$ or —COOY, wherein $R^4$ is hydrogen or $C_1$-$C_2$ alkyl and Y is an inorganic cation.

6. The method according to claim 5, wherein $R^1$ is hydrogen, $R^2$ is —$COCH_3$ and $R^3$ is hydrogen.

7. The method according to claim 5, wherein $R^1$ is methyl, $R^2$ is —$COCH_3$ and $R^3$ is hydrogen.

8. The method according to claim 6 or claim 7, wherein A is hydrogen, B is —$SO_3Y$ and G is —COOY, wherein Y is an inorganic cation.

9. The method according to claim 6 or claim 7, wherein A is —$SO_3Y$, B is hydrogen and G is —COOY, wherein Y is an inorganic cation.

10. The method according to claim 6 or claim 7, wherein A and B are —$SO_3Y$ and G is —COOY, wherein Y is an inorganic cation.

11. The method according to claim 7, wherein the compound of formula (I) is selected from the group consisting of:

12. The method according to claim 1 or claim 11, wherein the ligament is an articular ligament.

13. The method according to claim 1 or claim 11, wherein the ligament is a periodontal ligament.

14. The method according to claim 1 or claim 11, further comprising administering chondroitin sulphate.

15. The method according to claim 1 or claim 11, wherein the disease, disorder or injury is selected from the group consisting of tendinosis and bone loss.

16. The method according to claim 1 or claim 11, wherein the administering is by oral administration.

17. The method according to claim 1 or claim 11, wherein the administering is by intralesional administration.

18. The method according to claim 1 or claim 11, wherein the administering is by perilesional administration.

19. The method according to claim 1 or claim 11, wherein the administering is by administration in an implant.

20. The method according to claim 1 or claim 11, wherein the administering is by topical administration to an exposed tendon, ligament or periodontal bone.

21. The method according to claim 1, further comprising administering chondroitin sulphate and wherein the compound of formula (I) is selected from the group consisting of:

22. The method according to claim 1, wherein the method of treating a tendon, ligament or periodontal bone injury is a method of repairing or regenerating a tendon, ligament or bone injury.

23. The method according to claim 22, wherein the injury is the result of a trauma or an overuse.

24. The method according to claim 11, wherein the method of treating a tendon, ligament or periodontal bone injury is a method of repairing or regenerating a tendon, ligament or bond injury.

* * * * *